United States Patent [19]

Hauptly

[11] Patent Number: 4,855,706
[45] Date of Patent: Aug. 8, 1989

[54] ORGANIC LIQUID DETECTOR

[76] Inventor: Paul D. Hauptly, 4583 Mildred Dr., Fremont, Calif. 94536

[21] Appl. No.: 96,079

[22] Filed: Sep. 11, 1987

[51] Int. Cl.$^4$ .............................................. H01L 7/00
[52] U.S. Cl. ...................................... 338/34; 73/304 R
[58] Field of Search ................ 338/13, 34; 73/290 R, 73/304 R; 340/612, 618, 620

[56] References Cited

U.S. PATENT DOCUMENTS

| | | | |
|---|---|---|---|
| 3,907,717 | 9/1975 | Hebert | 338/13 X |
| 4,125,822 | 11/1978 | Perren et al. | 338/34 |
| 4,631,952 | 12/1986 | Donaghey | 338/34 X |
| 4,666,628 | 5/1987 | Uchikawa | 338/34 X |

Primary Examiner—C. L. Albritton
Attorney, Agent, or Firm—Rosenblum, Parish & Bacigalupi

[57] ABSTRACT

An electrical sensor and sensor material for detecting the presence of an organic liquid by contact that is not sensitive to the presence of organic vapors from the liquid. The sensor material includes a relatively large concentration of electrically conductive particles within a swellable matrix.

12 Claims, 4 Drawing Sheets

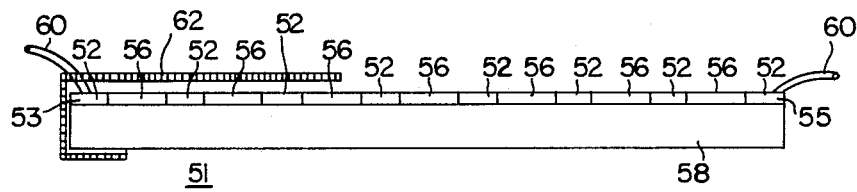
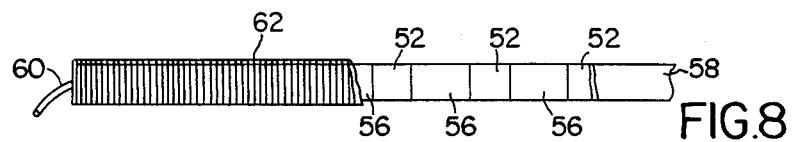
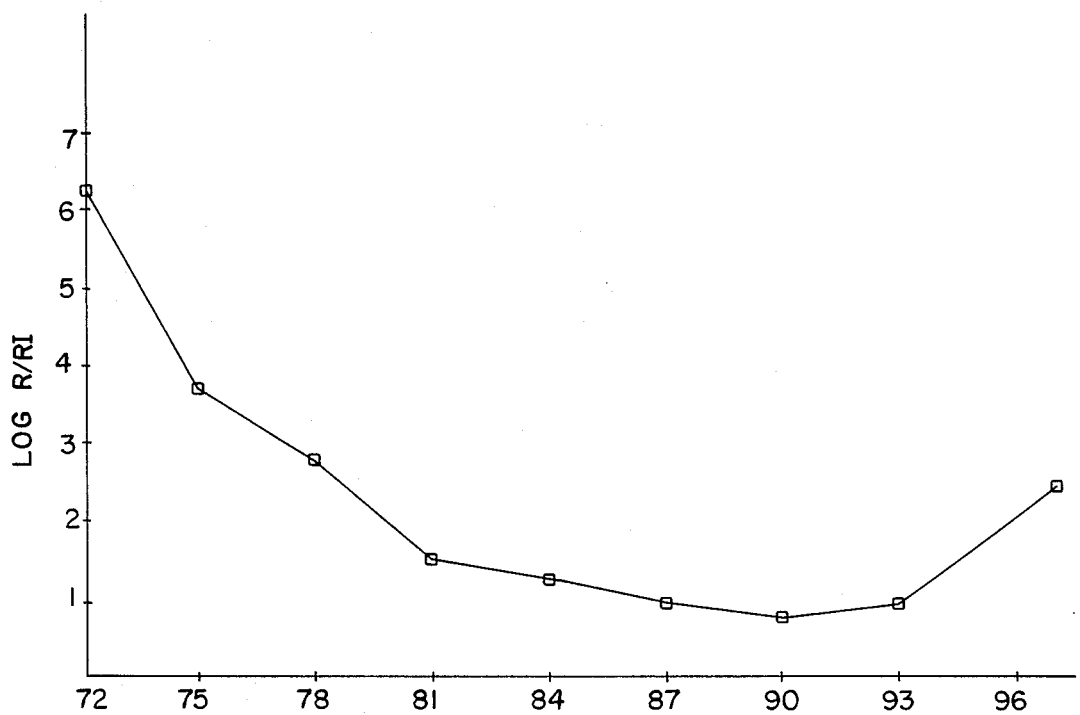
FIG.8
FIG.7
FIG.9

ORGANIC LIQUID DETECTOR

BACKGROUND OF THE INVENTION

1. Field of the Invention

This invention relates generally to devices for detecting liquids and more particularly to a detection device for organic liquids that has an electrically resistive sensor element which is sensitive to exposure to organic liquids.

2. Description of the Prior Art

The detection of organic liquids and particularly hydrocarbons such as fuels, solvents and reagents has long been commercially important. Many of these organic liquids are hazardous and knowledge of their presence can be useful in protecting property and the environment. In recent years the problem of hazardous organic liquids leaking from underground tanks and their associated piping has received a great deal of attention in both the public and private sectors. The ability to rapidly detect a leak of a variety of organic liquids from an underground source, with a minimum of ambiguity, is of great commercial and social importance.

Detectors have long been available which can detect organic vapors and gases and thereby imply the possible presence of an organic liquid. Catalytic combustion detectors, metal oxide semiconductor and flame combustion detectors are all examples of devices which can sense the presence of organic vapors and/or gases. However, these detectors cannot discern whether the source of the vapor or gas is local or remote, liquid or gaseous, a change in the "normal" background, the artifact of an old leak, or naturally occurring materials such as methane. Thus while alerting the user to the presence of an organic gas or vapor, they can be ambiguous as to its source. Also, some hydrocarbons such as motor oil produce little or no vapor and thus may fall below the threshold of vapor/gas sensors.

Organic liquids, such as motor fuels, are sometimes held in tanks constructed of fiberglass-reinforced plastic which use "double wall" construction. A desirable place to monitor such tanks for leakage is in the space between the inner and outer wall; the so-called "annulus". These tanks often outgas organic products used in their construction. The outgassed products may be detected by hydrocarbon vapor/gas sensors and so provide a rich and variable signal background which can lead to false alarms or the setting of detection thresholds so high that true leaks are not noted or are confused with false alarms.

Thermal conductivity devices can detect the presence of a liquid and, using appropriate techniques, can discriminate between organic liquids and other liquids. These devices can require a significant volume of the organic liquid be present, and are subject to error if partially in contact with another heat sink since they measure heat loss.

Float devices can also detect organic liquids, but must be combined with other devices to rule out other liquids such as water. Further, float devices must be installed in a way that takes gravity into account. Additionally, these devices may not discriminate between water and hydrocarbon/water mixtures such as acetone/water. They are relatively bulky and require a significant volume of liquid to alarm. Further, they often rely on the organic liquid floating on top of any water present. This would not be the case with products such as many halocarbon solvents.

Charles Ford in U.S. Pat. No. 2,691,134 and Lee Donaghey in U.S. Pat. No. 4,631,952 teach that rubbers, plastics and other swellable, electrically-insulating materials which have been loaded with particles of an electrically conductive material can be used to sense the presence of hydrocarbon liquids, vapors and gases. James Dolan et al. in U.S. Pat. No. 3,045,198 teach that conductive particles embedded onto the surface of a resilient, electrically-insulating substrate, such as a plastic or rubber, can be used to detect the presence of a hydrocarbon liquid, vapor and gas. However, these detectors fail to discriminate between liquids and high levels of vapors and gases.

The prior art detectors that are activated by both liquid and vapors or gas create uncertainty as to the source of the detected hydrocarbon, and the thermal conductivity and float devices require a significant volume of organic liquid before alarming. It would be very desirable to have a detector which could sense an organic liquid in very small amounts while not detecting vapors or gases. It would be desirable if this detector could operate at ambient temperature and not contain moving parts. Furthermore, it would be desirable to have a detector whose operation did not require electronic circuits which compensated for "background" levels of hydrocarbon gases and vapors.

SUMMARY OF THE INVENTION

It is an object of the present invention to provide a sensor material suitable for use in an organic liquid detector sensor, which material changes in its electrical resistance when physically contacted by an organic liquid but not by the vapor and/or gas of said liquid.

It is another object of the present invention to provide a sensor material which includes a mixture of electrically conductive particles and a matrix, said material being swellable upon contact with said liquid and not swellable upon contact with the vapor or gas of said liquid.

It is a further object of the present invention to provide a sensor material which returns from a swelled condition to an unswelled condition upon removal of contact with an organic liquid.

It is yet another object of the present invention to provide a sensor material which is easy to apply to a substrate to create a sensor.

It is yet a further object of the present invention to provide an organic liquid sensor which varies in its resistivity upon contact with an organic liquid, but does not significantly change its resistivity when contacted by the gas and/or vapor of said liquid.

It is still another object of the present invention to provide a sensor which utilizes a swellable sensor material to detect organic liquids but not the gas and/or vapor of said liquids.

It is still another object of the present invention to provide a sensor for detecting organic liquids which has no moving parts and is easy to manufacture and use.

The detector sensor material of the present invention comprises an electrically-insulating swellable matrix which has been rendered electrically conductive through its intimate admixture with electrically conductive particles. The sensor of the present invention includes a sensor material of the present invention disposed upon a solid substrate. A means for forming electrical contact with the electrically conductive matrix is provided. Upon exposure to an organic liquid such as a hydrocarbon, the matrix swells, thus increasing the spacing between some of the conductive particles, thereby causing a significant increase in electrical resistance of the sensor. By controlling the ratios of swellable matrix and conductive particles, the response of the sensor to vapors and gases can be greatly reduced, such that the sensor is sensitive to organic liquids but insensitive to the vapor or gas of those liquids. The proper ratios of materials comprising the sensor material further produces a sensor with very rapid response times and similarly rapid reset times. The sensor can be very small and made suitable for installation in small, nearly inaccessible spaces without regard to its position to gravity.

It is an advantage of the present invention that it provides a sensor material suitable for use in an organic liquid detector sensor, which material changes in its electrical resistance when physically contacted by an organic liquid but not by the vapor and/or gas of said liquid.

It is another advantage of the present invention that it provides a sensor material which includes a mixture of electrically conductive particles and a matrix, said material being swellable upon contact with said liquid and not swellable upon contact with the vapor or gas of said liquid.

It is a further advantage of the present invention that it provides a sensor material which returns from a swelled condition to an unswelled condition upon removal of contact with an organic liquid.

It is yet another advantage of the present invention that it provides a sensor material which is easy to apply to a substrate to create a sensor.

It is yet a further advantage of the present invention that it provides an organic liquid sensor which varies in its resistivity upon contact with an organic liquid, but does not change its resistivity when contacted by the gas and/or vapor of said liquid.

It is still another advantage of the present invention that it provides a sensor which utilizes a swellable sensor material to detect organic liquids but not the gas and/or vapor of said liquids.

It is still another advantage of the present invention that it provides a sensor for detecting organic liquids which has no moving parts and is easy to manufacture and use.

IN THE DRAWING

FIG. 7 is a side view of yet another preferred embodiment of the present invention;

FIG. 8 is a top plan view, having a cutaway section of the device depicted in FIG. 7; and FIG. 9 is a graphic representation of the performance of the present invention.

DETAILED DESCRIPTION OF THE PREFERRED EMBODIMENTS

Figure 1:
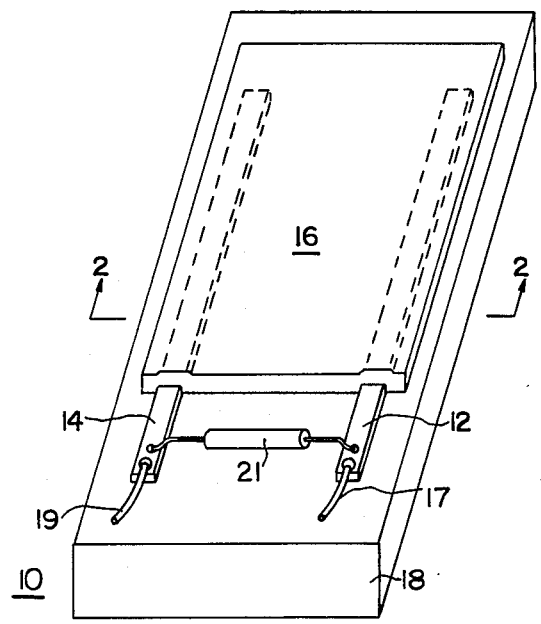
FIG. 1 is a perspective view of a preferred embodiment of a sensor of the present invention, having the sensor material of the present invention disposed thereon.
Figure 2:
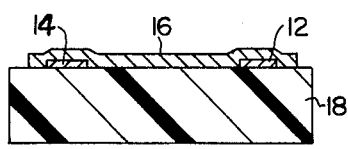
FIG. 2 is a side cross-sectional view of the device depicted in FIG. 1, taken along lines 2—2 thereof.

A first preferred embodiment of the sensor 10 of the present invention is shown in FIGS. 1 and 2. As depicted in FIGS. 1 and 2, the sensor 10 includes two electrodes 12 and 14 that are disposed upon the surface of a non-conductive substrate 18. The substrate should be sufficiently rigid to prevent bending which could affect the sensor 10. A resistive sensing material 16 is disposed upon the substrate 18 and electrodes 12 and 14 in such a manner as to form an electrical connection between the two electrodes 12 and 14. Two wires 17 and 19 are attached to electrodes 12 and 14 respectively as an electrical connection means. Optionally, an electrical resistor 21 of known value is connected across electrodes 12 and 14 to provide information about the presence of the sensor device in a measurement circuit, and also to provide information about the position of the device in a system with a plurality of said devices. The ends of the wires 17 and 19 are to be connected to a detector circuit (not shown) which is capable of detecting changes in the resistance of the sensor 10 caused by changes in the resistivity of the sensing material 16.

The monitoring of the resistance change of the sensor can be accomplished using Wheatstone bridges, comparators, window comparators, sliding comparators and ohmmeters. The circuits shown in U.S. Pat. Nos. 2,691,134, and 3,045,198 and 4,631,952 are also suitable. It will be apparent to one skilled in the art that there are a myriad of additional ways of monitoring the change in resistance of the resistive sensor.

The resistive sensing material 16 includes a matrix that is intimately admixed with electrically conductive particles. The particles should be significantly more conductive than the matrix. The matrix must be swellable on contact with the liquid(s) to be monitored, and non-swellable on contact with other liquids. It is preferred that the matrix swell in a reversible manner, so that upon removal of the liquid, the sensor returns to its original resistance value. The matrix should be an electrical insulator and it should not decompose or dissolve in the liquid of interest. It is also desirable that the matrix and conductive particles be stable in each other's presence and stable over the course of time. Examples of suitable matrix base materials are silicone rubber, synthetic rubber, polyvinyl chloride, and the like. While elastomers and plastics have been emphasized, natural polymers such as waxes and proteins could be employed as the base material of the matrix. Silicone rubber is preferred for the detection of hydrocarbons and organic liquids. It may be desirable to use fillers in the matrix along with the base material. This can be done to reinforce the matrix or reduce the conductivity of the sensing material at some percent swelling so as to accentuate a change in resistance which otherwise might be electrically unnoticeable, or simply to reduce the product's cost. An example of such a filler is talc.

The electrically-conductive particles should be relatively inert in service, significantly more conductive than the matrix, and small enough to provide easy mixing with the matrix and minimize abrasion to the matrix on swelling. They should also provide stable electrical conductivity under operating conditions, and they should not catalyze reactions between the expected atmosphere and either the matrix or the expected liquid(s). Examples of conductive particles are: powdered graphite, crystalline graphite, carbon black, copper, nickel and the like, as well as objects such as microspheres coated with such conductive materials. Particulate sizes from 50 to 300 microns have proven to be acceptable. Crystalline graphite, formed in small slender crystals, is the preferred electrically-conductive particulate; however, powdered graphite has proven to be quite acceptable.

The optimum volume percent of conductive particles in the sensor 16 (as computed from published densities) is from approximately 87 percent to approximately 93 percent; however, the overall range for acceptable devices is from approximately 78 percent to approximately 97 percent. As the volume percent of conductive particles increases, the vapor sensitivity decreases. However, as the volume percent of conductive particles increases, the brittleness of the sensor element 16 increases as well. Mixtures above 97 percent conductive particles become brittle, fragile, and difficult to apply.

A preferred sensor material is prepared by taking approximately 20 grams of xylene and mixing into it 9.4 grams of powdered graphite, such as the graphite from Superior Graphite Co. "Micromesh Graphite Powder" (97 to 300 mesh) and then adding 0.6. grams of silicone rubber, such as that provided from General Electric Company, brand "Silicone II" Household Glue and Seal. Silicone II is a trademark of the General Electric Company. The mixture is agitated until the silicone dissolves and is uniformly mixed with the graphite. The percent by volume of conductive particles in the resultant coating of this example is approximately 90 percent.

Another example of a suitable sensor material can be formulated using the technique described in the above example by taking approximately 20 grams of xylene and mixing into it 1.5 grams of talc and 8.0 grams of "Micromesh Graphite Powder" and 1.0 grams of "Silicone II". The percent by volume of conductive particles in the resultant coating of this example is approximately 75 percent.

A particular example of the present invention in the form depicted in FIGS. 1 and 2 is constructed utilizing a printed circuit board as a substrate 18 which has been etched to leave two metallic traces as electrodes 12 and 14. The electrodes 12 and 14 are each approximately 0.025 inches wide and approximately 0.5 inches long; they are oriented parallel to each other and spaced approximately 0.1 inches apart. Wires 17 and 19 used to connect the device to a measurement or alarm circuit, are soldered at one end of the board 18 to each of the electrodes 12 and 14 respectively. The board is then masked for coating with the sensor material 16 such that the only exposed area is the unsoldered area of the two electrodes and the surface of the substrate 18 area between the electrodes 12 and 14. Thereafter, the unmasked area of the substrate and electrodes is coated with the sensor material by spraying, brushing, printing, dipping or the like, and the mixture is allowed to dry and/or cure. Spraying is the preferred coating method. A single thin coating of approximately 0.0005 to 0.05 inches is preferred. This construction is by way of example, and it will be apparent to those ordinarily skilled in the art that other substrates, electrodes, matrices, conductive particles, ratios of matrix to particles within the ranges given above, coating techniques and thicknesses will produce useful sensors.

Figure 3:
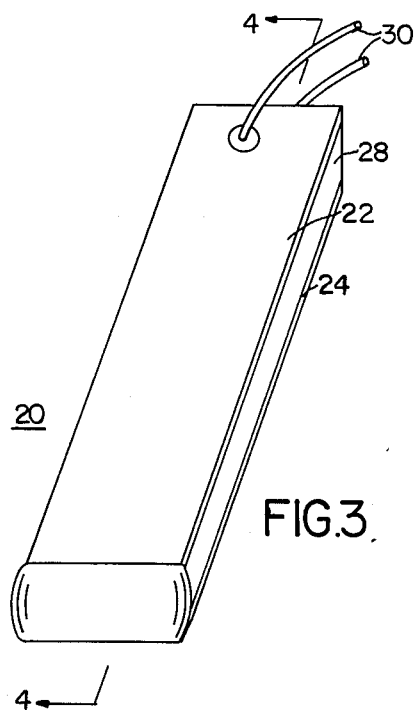
FIG. 3 is a perspective view of another preferred embodiment of the present invention.
Figure 4:
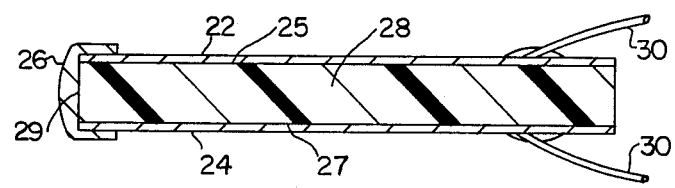
FIG. 4 is a side cross-sectional view of the device depicted in FIG. 3, taken along lines 4—4 thereof.

FIGS. 3 and 4 illustrate an alternative sensor embodiment. The sensor 20 consists of a flat insulator substrate 28 which has electrodes 22 and 24 disposed on two parallel surfaces 25 and 27 of the substrate 28. The sensor coating 26 is then applied to a surface 29 of the substrate 28 perpendicular to and between the electrodes 22 and 24 in such a manner as to provide a connection means between the electrodes. Wires 30 are attached to each of the electrodes to provide a means of connecting the sensor to a measurement or alarm circuit.

Figure 5:
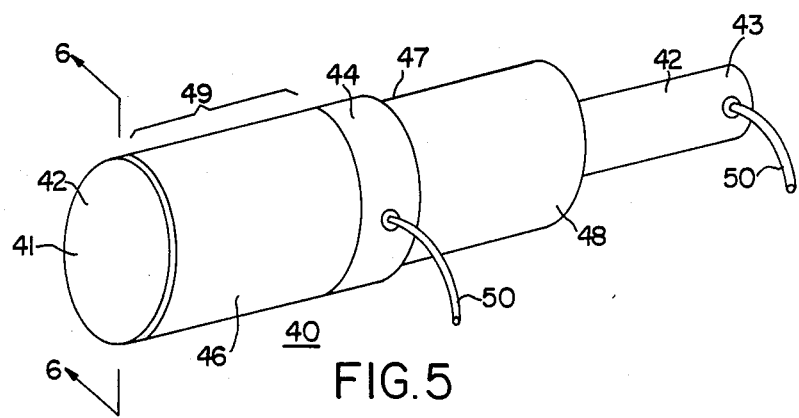
FIG. 5 is a perspective view of a further preferred embodiment of the present invention.
Figure 6:
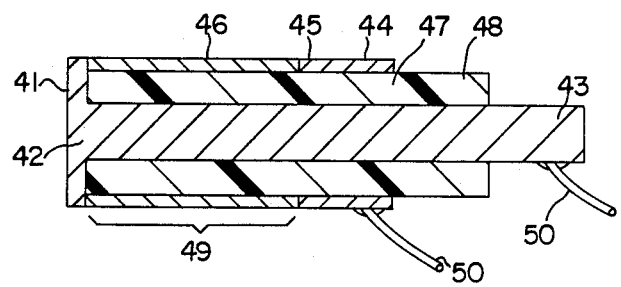
FIG. 6 is a side cross-sectional view of the device depicted in FIG. 5, taken along lines 6—6 thereof.

FIGS. 5 and 6 illustrate a further alternative sensor embodiment 40 of the invention. A first electrode 42 consists of a conductive material formed in a disk shaped end portion 41 from which projects cylindrical portion 43 that projects perpendicularly to and is centered upon a flat surface of the disk portion 41. The cylindrical portion 43 of the conductor 42 is electrically continuous with the disk. Located over part of the first electrode 42 is an insulating substrate 48 that is shaped as a hollow cylinder having an inside diameter that closely matches the outside diameter of the cylindrical portion 43 of electrode 42. The outside diameter of the insulator 48 closely matches the diameter of the disk portion 41 of electrode 42. One end of the substrate 48 is in flush contact with the disk 41. Disposed over and around part of the second end 47 of the insulating substrate 48 is a hollow, cylindrically shaped second electrode 44 which is located so as to leave a gap 49 between the disk portion 41 of electrode 42 and the nearest edge 45 of the second electrode 44. A layer of sensor material 46 is then applied to the outer surface of the insulating substrate 48 in such a manner as to provide an electrical connection between the disk portion 41 of the first electrode 42 and the near end 45 of the second electrode 44. Wires 50 are then attached to the cylindrical portion 43 of electrode 42 and to the second electrode 44 to provide a means of electrical connection to a measurement or alarm circuit.

FIGS. 7 and 8 depict a further preferred embodiment 51 which provides for an elongated resistive sensor that is useful for monitoring areas or lengths rather than discrete points. An insulator substrate 58 is alternately striped with a conductor 52 and sensor coating 56. The beginning and ending strips are formed with the conductors 53 and 55 which act as the electrodes and for the attachment of wires 60. The alternations of the conductor strips 52 and sensor strips 56 are repeated as often as needed to provide the length of the sensor desired. Additionally, the width of the conductors 52 and sensor coating 56 can be varied to provide long lengths of conductor 52 relative to sensor lengths 56 where sensor element resistance might otherwise accumulate to a value high enough to be less useful. Conversely, the widths may be varied to provide relatively large sensor areas which could be relatively insensitive to a small amount of liquid, thus providing a quantitative aspect to the sensor with regard to the volume of liquid required to significantly change its resistance. Such a sensor 51 would be useful to encircle an area, thus providing full coverage of an area rather than relying on point sensors.

An optional mechanical shield 62, shown as a screen material in FIGS. 7 and 8, may be provided to protect the sensor surface from mechanical abuse. Such a mechanical shield 62 may be attached to any of the embodiments described herein. However, the shield must either be permiable to the liquid or leave portions of the sensor exposed to allow liquid contact.

FIG. 9 illustrates the effect, after 100 days' exposure, of a saturated, unleaded gasoline vapor in air on sensors of the type depicted in FIGS. 1 and 2 constructed using from 72 percent to 97 percent powdered graphite (vol:vol) in a silicone rubber base material matrix made in accordance with the particular examples described hereinabove. In FIG. 9, RI is the initial sensor reading and R is the final sensor reading. The results illustrate that a minimum change in resistance, as a response to vapor, occurs over the range of 78 percent to 97 percent graphite and that the optimum is from about 87 percent to about 93 percent graphite.

While the above descriptions contain many specific examples, these should not be construed as limitations on the scope of the invention, but rather as examples of some preferred embodiments thereof. Many other variations are possible. For example, the device of FIGS. 1 and 2 could be rolled into a cylindrical configuration, as could the device of FIGS. 7 and 8. Such modifications, which would be obvious to one skilled in the art, are contemplated and within the scope of this invention. Accordingly, the scope of the invention should not be determined by the embodiments illustrated, but by the appended claims and their legal equivalents.

What I claim is:

1. An organic liquid sensor comprising:
   a sensor means for sensing the contact thereto by an organic liquid and distinguishing the contact thereto by a vapor or gas of said liquid including;
   a non-conductive substrate;
   at least two electrodes being disposed proximate said substrate such that said substrate holds said electrodes in electrical separation; said electrodes being formed for electrical connection to a detector circuit;
   a sensor material being disposed upon said substrate and contacting said electrodes so as to form an electrical connection between said electrodes;
   said sensor material including a uniform mixture of electrically-conductive particles with a non-conductive matrix, said sensor material having a sufficient quantity of said particles such that said sensor material is capable of swelling upon contact with said liquid but not upon contact with the vapor or gas of said liquid; and
   wherein the percent by volume of said electrically-conductive particles in said sensor material varies from approximately 78 percent to 97 percent.

2. An organic liquid sensor comprising:
   a sensor means for sensing the contact thereto by an organic liquid and distinguishing the contact thereto by a vapor or gas of said liquid including;
   a non-conductive substrate;
   at least two electrodes being disposed proximate said substrate such that said substrate holds said electrodes in electrical separation; said electrodes being formed for electrical connection to a detector circuit;
   a sensor material being disposed upon said substrate and contacting said electrodes so as to form an electrical connection between said electrodes;
   said sensor material including a uniform mixture of electrically-conductive particles with a non-conductive matrix, said sensor material having a sufficient quantity of said particles such that said sensor material is capable of swelling upon contact with said liquid but not upon contact with the vapor or gas of said liquid; and
   wherein the percent by volume of conductive particles in said sensor material varies from approximately 87 percent to approximately 93 percent.

3. The device as described in claim 1 or 2 wherein said matrix includes a material selected from the group consisting of silicone rubber, synthetic rubber, polyvinyl chloride, wax, proteins, and mixtures thereof.

4. The device as described in claims 1, or 2 wherein said electrically-conductive particles include a material selected from the group consisting of powdered graphite, crystalline graphite, carbon black, copper, nickel, microspheres coated with the previously mentioned materials, and mixtures thereof.

5. The device as described in claim 1 or 2 wherein said matrix includes a non-conductive filler material.

6. The device as described in claim 5 wherein said substrate is formed from a printed circuit board material and said electrodes are formed as metallic traces disposed thereon, and said sensor material is disposed as a coating that covers portions of said electrodes and said substrate between said electrodes.

7. The device as described in claim 6 wherein said sensor material is disposed upon said substrate in a coating having a thickness of from approximately 0.0005 inches to approximately 0.05 inches.

8. A sensor material having the property that its electrical resistance is altered upon contact thereto with an organic liquid but not upon contact thereto with the vapor or gas of said liquid comprising:
   a quantity of electrically-conductive particles;
   a quantity of non-conductive matrix material;
   said particles and said matrix material being uniformly mixed together;
   said sensor material having a sufficient quantity of said particles such that said sensor material is capable of swelling upon contact with said liquid but not upon contact with the vapor or gas of said liquid; and
   wherein the percent by volume of said electrically-conductive particles in said sensor material varies from approximately 78 percent to 97 percent.

9. A sensor material having the property that its electrical resistance is altered upon contact thereto with an organic liquid but not upon contact thereto with the vapor or gas of said liquid comprising:
   a quantity of electrically-conductive particles;
   a quantity of non-conductive matrix material;
   said particles and said matrix material being uniformly mixed together;
   said sensor material having a sufficient quantity of said particles such that said sensor material is capable of swelling upon contact with said liquid but not upon contact with the vapor or gas of said liquid; and
   wherein the percent by volume of conductive particles in said sensor material varies from approximately 87 percent to approximately 93 percent.

10. The material as described in claims 8 or 9 wherein said matrix includes a material selected from the group consisting of silicone rubber, synthetic rubber, polyvinyl chloride, wax, proteins, and mixtures thereof.

11. The material as described in claims 8 or 9 wherein said electrically-conductive particles include a material selected from the group consisting of powdered graphite, crystalline graphite, carbon black, copper, nickel, microspheres coated with the previously mentioned materials, and mixtures thereof.

12. The material as described in claims 8 or 9 wherein said matrix includes a filler material.

* * * * *